United States Patent
Shi et al.

(10) Patent No.: US 12,383,616 B2
(45) Date of Patent: Aug. 12, 2025

(54) RECOMBINANT HERPES ZOSTER VACCINE COMPOSITION AND APPLICATION THEREOF

(71) Applicant: IMMUNE-PATH BIOTECHNOLOGY (SUZHOU) CO., LTD., Suzhou (CN)

(72) Inventors: Li Shi, Shanghai (CN); Zhi Zhang, Shanghai (CN); Wenli Tian, Shanghai (CN); Lin Liu, Shanghai (CN); Xiaodong Sun, Shanghai (CN); Wei Yang, Shanghai (CN); Wei Li, Shanghai (CN)

(73) Assignee: IMMUNE-PATH BIOTECHNOLOGY (SUZHOU) CO., LTD., Jiangsu (CN)

( * ) Notice: Subject to any disclaimer, the term of this patent is extended or adjusted under 35 U.S.C. 154(b) by 742 days.

(21) Appl. No.: 17/623,525

(22) PCT Filed: Jun. 24, 2020

(86) PCT No.: PCT/CN2020/098179
§ 371 (c)(1),
(2) Date: Dec. 28, 2021

(87) PCT Pub. No.: WO2020/259609
PCT Pub. Date: Dec. 30, 2020

(65) Prior Publication Data
US 2022/0347293 A1    Nov. 3, 2022

(30) Foreign Application Priority Data
Jun. 28, 2019 (CN) .......... 201910574549.4

(51) Int. Cl.
| | | |
|---|---|---|
| *A61K 39/25* | (2006.01) | |
| *A61K 39/39* | (2006.01) | |
| *A61P 31/22* | (2006.01) | |
| *A61P 37/04* | (2006.01) | |
| *C12N 1/00* | (2006.01) | |
| *A61K 39/00* | (2006.01) | |

(52) U.S. Cl.
CPC .............. *A61K 39/25* (2013.01); *A61K 39/39* (2013.01); *A61P 31/22* (2018.01); *A61P 37/04* (2018.01); *A61K 2039/55505* (2013.01); *A61K 2039/55561* (2013.01)

(58) Field of Classification Search
None
See application file for complete search history.

(56) References Cited

U.S. PATENT DOCUMENTS

| | | | |
|---|---|---|---|
| 2020/0270637 A1* | 8/2020 | Chan | C12N 15/86 |
| 2021/0187099 A1* | 6/2021 | Nam | C07K 14/005 |

FOREIGN PATENT DOCUMENTS

| | | |
|---|---|---|
| CN | 105214083 A | 1/2016 |
| CN | 108472309 A | 8/2018 |
| CN | 109602901 A | 4/2019 |

OTHER PUBLICATIONS

Olson et al. (Journal of Virology, 1997, p. 110-119).*
Zhan N et al., Enhancement of Humoral immunity in the mouse by coupling CpG and aluminium to the HCV recombinant immunogen, Letters in Biotechnology, Nov. 2011, pp. 777-780, vol. 22, No. 6.
Haumont M et al., Purification, characterization and immunogenicity of recombinant varicella-zoster virus glycoprotein gE secreted by Chinese hamster ovary cells, Virus Research, 1996, pp. 199-204, 40 (2), Elsevier.
First Office Action of priority document CN 201910574549.4 on Sep. 10, 2021.

* cited by examiner

*Primary Examiner* — Agnieszka Boesen
(74) *Attorney, Agent, or Firm* — IP & T GROUP LLP

(57) ABSTRACT

Disclosed in the present invention are a recombinant herpes zoster vaccine composition and an application thereof. Compared with other combinations of antigens and adjuvants, the novel vaccine composition provided by the present invention has a more beneficial immune effect.

4 Claims, No Drawings

RECOMBINANT HERPES ZOSTER VACCINE COMPOSITION AND APPLICATION THEREOF

This application is a National Phase application of PCT application no. PCT/CN2020/098179 filed on Jun. 24, 2020, which claims the priority of the Chinese patent application filed with the Chinese Patent Office on Jun. 28, 2019, with the application number CN 201910574549.4 and entitled "Recombinant Herpes Zoster Vaccine Composition and Application Thereof", the entire content of which is incorporated herein by reference.

TECHNICAL FIELD

The present disclosure pertains to the field of biomedicine. Specifically, the present disclosure relates to a novel recombinant herpes zoster vaccine composition and application thereof.

BACKGROUND ART

Varicella zoster virus (VZV), also called human herpesvirus-3, is one of the eight human herpes viruses. Varicellazoster virus spreads all over the world and is highly contagious. So far, only one serotype has been found. In nature, VZV only infects human and can cause chickenpox and herpes zoster (HZ), with the chickenpox commonly seen in children and the herpes zoster only occurring in adults. After the primary infection with chickenpox, the virus becomes latent in ganglia of the host. With age, immune function impairment or immunosuppression, VZV can be reactivated and cause herpes zoster. The clinical manifestation of herpes zoster is a unilateral vesicular rash, which is characterized by being confined to a single skin segment, and is usually accompanied by radicular pain. Patients with herpes zoster may have obvious pain and discomfort. Symptoms may last for several weeks or months, and in severely ill patients, even for several years, leading to a decline in the quality of life. In rare cases, herpes zoster may not cause a rash. Complications occur in about 25% of people with herpes zoster, which number increases with age. The most common and serious complication is post-herpetic neuralgia (PHN), that is, pain that persists after the acute phase of herpes. The incidence of PHN in patients with herpes zoster is 10% to 30%. The pain may persist for several months or even years, which seriously affects the quality of life of patients. The risk factors that affect the onset of herpes zoster are age, immune function deficiency, gender, and other potential factors.

Most primary VZV infections occur in children, after which VZV becomes latent in the ganglia, and VZV can be reactivated in adults. Studies have shown that about 99% of Americans aged 40 and above have serological evidence of VZV infection; 90% of Europeans aged 20-29 years are seropositive for anti-VZV; and in South America, Australia, and some countries in Asia, the primary VZV infection may occur later, but 90% of people over the age of 40 are VZV seropositive. Therefore, on a global scale, the vast majority of adults are at risk of developing herpes zoster and its related complications. The global incidence of herpes zoster is (3-5)/1000 persons per year. In Asia-Pacific region, the incidence is (3-10)/1000 persons per year, which is increasing by 2.5% to 5.0% each year, the hospitalization rate is (2-25)/100,000 persons per year, the death rate is (0.017-0.465)/100,000 persons per year, and the recurrence rate is 1% to 6%. At present, China is in a severe condition of population aging, and the social and economic burden brought by HZ is increasing year by year. For individuals, HZ has brought a huge negative impact on the quality of life of patients, especially elderly patients. According to data released by the National Bureau of Statistics, it is estimated that the population over 40 years old in 2017 is about 650 million. If the incidence rate of HZ is 2.5/1000 persons per year, the number of new cases of HZ in China are conservatively estimated to be about 1.6 million each year.

Since medication can only relieve symptoms, vaccination is the best strategy to prevent HZ and its complications. Currently, only two HZ vaccines are commercially available (Zostavax, a HZ live attenuated vaccine, and Shingrix, a HZ subunit vaccine). Zostavax, available from MSD, is a live attenuated vaccine, and contains the same virus strain as the VZV Oka strain used in the varicella vaccine. The vaccine formula contains a minimum potency of 19400 PFU. Zostavax was approved by the FDA in 2006 and has been approved in more than 60 countries. One dose can be subcutaneously administered to people 50 years of age or older. Shingrix developed by GlaxoSmithKline is a subunit vaccine based on recombinant gE protein supplemented with a novel adjuvant $AS01_B$. Phase III clinical trial data showed that this subunit vaccine has better immunogenicity and effectiveness than those of Zostavax in the elderly. Shingrix was approved by the FDA in 2017. It is suitable for people 50 years of age or older and requires 2 doses. Currently, Shingrix has been conditionally approved to be marketed in China. Domestic vaccines under development are all live attenuated vaccines, and their protective efficacy and immunity durability are lower than those of Shingrix. Shingrix is out of stock due to issues such as production capacity, and there thus is an urgent need in China for a self-developed subunit vaccine that helps reduce the burden of diseases caused by herpes zoster and its complications.

VZV-specific immune response is essential to reduce the incidence of herpes zoster and post-herpetic neuralgia. Shingrix developed by GlaxoSmithKline, a subunit vaccine based on the novel adjuvant $AS01_B$ that plays a key role in this vaccine, has been proven to be effective in preventing herpes zoster and neuralgia associated therewith. Therefore, choosing a suitable adjuvant to develop a vaccine can improve the cellular immune and humoral immune responses in the target population, thereby effectively preventing herpes zoster. $AS01_B$ adjuvant system available from GlaxoSmithKline contains liposomes, MPL, and QS-21, and can cause a strong cellular immune response. However, MPL and QS-21 are currently limited by source and have limited production scale, and domestic conditions for large-scale production of this adjuvant system are incomplete and unable to meet the needs of subsequent clinical application. However, CpG ODN can be produced on a large scale through chemical synthesis, for which quality control is easy. CpG ODN is an agonist of Toll-like receptor 9 (TLR9), which can stimulate cells expressing TLR9 and activate downstream pathways in innate immune response. CpG ODN, on the one hand, induces the expression of type I interferon and inflammatory factors, and on the other hand, matures plasmacytoid dendritic cells, thereby enhancing humoral immune and cellular immune responses. An aluminum adjuvant is by far the most widely used human vaccine adjuvant, and a combined adjuvant of an aluminum adjuvant and another adjuvant also has a wide range of applications. A combined adjuvant of an aluminum adjuvant and CpG 7909 is used in both hepatitis B and malaria preventive vaccines that have passed phase II clinical trials.

Although some vaccines against VZV have been developed in the prior art, there are still problems such as low expression efficiency of VZV protein, low activity of the protein obtained by expression, and unsatisfactory immune effect as well as limitation in supplies of adjuvant materials. Therefore, there is a need to develop improved VZV vaccine products in this field. From a strategic point of view, there is always a need for novel compositions or vaccines with immunogenicity improved by attempts and improvements for adjuvants or formulation combinations to increase immune response.

SUMMARY

In one aspect of the present disclosure, a recombinant herpes zoster preventive vaccine is provided, which contains an antigen against varicella zoster virus (VZV). More specifically, the aforementioned antigen may be VZV gE protein.

The VZV described herein is a double-stranded DNA virus with only one serotype. Its genome is about 125,000 bp in length, encodes 71 genes, and finally expresses 67 different proteins, including 7 glycoproteins (gp I to gp VI), respectively named gE, gB, gH, gI, gC, gK, and gL. Among them, glycoprotein E (gE protein) is the main surface structure protein of VZV and the most important neutralizing antigen, and has high conservation. Specifically, the VZV glycoprotein E is encoded by 0RF68 and consists of 623 amino acids, and is a type I transmembrane glycoprotein. Glycoprotein E is most abundantly expressed on the surface of viruses and infected cells, and has both T- and B-cell epitopes. Therefore, VZV-gE is most extensively studied, and is expected to become an antigen in a new generation of subunit varicella or herpes zoster vaccines.

Existing studies on VZV gE protein shows that the protein molecule of wild-type VZV gE includes four regions, namely a signal peptide, an extracellular region, a transmembrane region, and an intracellular region. The three antigenic determinants of VZV gE are all distributed in the extracellular region (refer to, for example, Grose C. Glycoproteins encoded by varicella-zoster virus: biosynthesis, phosphorylation, and intracellular trafficking. Annu Rev Microbil. 1990, 44: 59-80.). In the NCBI database, there are many existing gE protein sequences (for example, amino acid sequences with the following Sequence IDs: Q9J3M8.1, AQT34120.1, AGY33616.1, AEW88548.1) for those skilled in the art to choose. The inventors of the present disclosure retrieved, from NCBI, a total of 25 full-length sequences of VZV gE protein, which are derived from different virus strains. The results of amino acid sequence analysis and alignment show that the protein sequences of 7 virus strains (AAK19946.1, AHB80298.1, Q9J3M8.1, ABE67176.1, AGL51024.1, AFO85645.1, and ABF22079.1) are identical, and each site is the most conservative. Therefore, all these sequences can be used as the ideal basis for gE antigen protein selection.

Meanwhile, considering factors such as the influence of the hydrophobic transmembrane region on the expression of foreign proteins, the modification methods for gE protein are also mature. For example, in order to increase the expression level of a protein, the transmembrane region (hydrophobic region) and intracellular region are generally removed (for example, patent CN102517302A). Meanwhile, when translating a mutant protein precursor using a translation mechanism in a carrier cell (host cell) and transferring it to the cell membrane to be secreted outside the cell, a signal peptide region is usually cut by signal peptidase (for example, patents CN102548578A, CN102711812B, and literatures cited by GSK). As a conventional technical means in the art, the transmembrane region, intracellular region, and signal peptide can be predicted by related application software. For example, SignalP (http://www.cbs.dtu.dk/services/SignalP/) may be used for predictive analysis of whether the protein has a signal peptide, TMHMM Server V.2.0 software is used to predict the transmembrane region of a protein, and PSORT software is used to determine the accuracy of the secreted signal peptide and whether the cleavage site of the signal peptide can be identified and cleaved.

For the purpose of developing the present disclosure, in examples of the present disclosure, NCBI accession number ID: Q9J3M8.1 is used as the basis, and the C-terminal 77 amino acids are truncated (removal of the transmembrane region and intracellular region) to obtain a model antigen (N-terminal 1-30 amino acids are signal peptide).

The above-mentioned antigens can be easily obtained by conventional technical means of modern molecular biology. A typical method includes a method of expressing the above-mentioned gE protein in CHO cells, which includes the steps of:
(1) cloning the gE gene of the present disclosure into an expression vector;
(2) transforming the expression vector obtained in step (1) into CHO cells;
(3) obtaining a cell line stably expressing gE protein, through screening of mini cell populations and monoclonal screening; and
(4) using the cell line obtained in step (3) for expression to obtain a VZV gE protein.

The protein obtained above is subjected to a conventional processing method, such as hydrophobic chromatography, anion exchange chromatography, hydroxyapatite chromatography, ultrafiltration, or nanofiltration, to obtain an antigen protein with a purity of more than 95%.

It should be noted that the method of stably expressing VZV gE recombinant protein in CHO cell lines is a well-known method in the art. For details, refer to "Molecular Cloning: A Laboratory Manual" and other literatures, such as Haumont M, et al., Virus Research 40 (1996), 199-204, Purification, characterization and immunogenicity of recombinant varicella-zoster virus glycoprotein gE secreted by Chinese hamster ovary cells. Those skilled in the art may also choose other expression methods such as *Escherichia coli, Pichia* yeast, etc. to obtain gE protein (for example, refer to patent CN108315344A or CN107022559A for further introduction on gE protein preparation).

In a preferred embodiment, the vaccine composition further includes a pharmaceutically acceptable combined adjuvant (carrier). In a preferred embodiment, the pharmaceutically acceptable combined adjuvant is an aluminum adjuvant combined with a CpG ODN adjuvant. The inventors of the present disclosure surprisingly found that the combination of the above two adjuvants and gE protein shows surprisingly high immunological activity. Therefore, the vaccine composition of the present disclosure becomes a new generation of varicella zoster vaccine.

The aluminum adjuvant of the present disclosure is currently the most widely used type of adjuvant in vaccines. It has a history of more than 80 years of application and has been used by tens of billions of people. It was once the unique adjuvant approved by the U.S. Food and Drug Administration (FDA) for use in human vaccines. At present, there have been many studies on the use of aluminum adjuvants in vaccines. More systematic studies can be found in, for example, Chapter 8 "Adjuvant properties of aluminum and calcium compounds" and Chapter 9 "Structure and properties of aluminum adjuvants" in the book "Vaccine Design: The Subunit and Adjuvant Approach" (ISBN: 0-306-44867-X), or for example Chapter 4 "Use of aluminum compounds as vaccine adjuvants" in the book "Vaccine Adjuvants: Preparation Methods and Research Protocols" (ISBN: 1-59259-083-7). There have been some commercial aluminum adjuvants available for use in vaccines, including but not limited to Alhydrogel® (aluminum hydroxide) and Adju-Phos® (aluminum phosphate). The foregoing studies have also described preparation methods of aluminum adjuvants, and those skilled in the art can thus prepare a desired aluminum adjuvant and apply it in vaccine formulations as needed.

The CpG ODN adjuvant is a class of immunostimulatory oligopeptides known to have adjuvant properties, and can activate B cells, NK, dendritic cells (DC), etc. and induce the release of IL-12 and IFN-γ, thereby inducing a strong Th1-type response and cellular immunity. This type of adjuvant is also well-known to those skilled in the art, and has been described in the prior art, for example, in international applications such as WO 96/02555 and WO 99/33488. There are currently some commercialized CpG ODN adjuvants, such as CpG 7909 (Coley Company) or CpG 1018 (Dynavax Company). Of course, those skilled in the art can also design artificial synthetic sequences as needed.

For the specific preparation method of the vaccine formulation provided by the present disclosure, refer to, for example, the book "Vaccine Design: The Subunit and Adjuvant Approach" (ISBN: 0-306-44867-X). As one of the most conventional methods, the preparation method provided by the present disclosure involves mixing the aforementioned antigen protein of the present disclosure with the aforementioned pharmaceutically acceptable combined adjuvant. As a more specific example, in a preferred embodiment, the gE protein should preferably be adsorbed on the aluminum adjuvant. At the same time, the CpG ODN adjuvant is also preferably adsorbed on the aluminum adjuvant.

Regarding the general principle of dosage selection of vaccine formulations, the amount of each dose of vaccine should be able to cause an immune protective response in the vaccinated person without significant toxic side effects. Generally, the dosages of different antigen proteins are slightly different, and the optimal dosage of a particular vaccine can be determined by observing the antibody titer and other reactions of the subject. The vaccine formulation provided by the present disclosure has an antigen protein content of approximately 10-100 μg and more preferably 50-100 μg, an aluminum adjuvant content of approximately 100-600 μg and more preferably 225-600 μg, and a CpG ODN adjuvant content of approximately 50-1200 μg and more preferably 300-900 μg.

In a second aspect of the present disclosure, application of the aforementioned vaccine composition is provided for prevention or treatment of diseases or disorders associated with herpes zoster virus infection.

In a third aspect of the present disclosure, provided is a kit including a vaccine administration device, including but not limited to a needle device, a liquid ejection device, a powder device, and a spray device. The selection of the devices mainly depends on different modes of administration. Common modes of administration include intramuscular injection, intraperitoneal injection, intradermal injection or subcutaneous injection, or oral/digestive tract, respiratory tract and genitourinary tract mucosal administrations. The vaccine of the present disclosure may usually be injected intramuscularly, and the common administration device is a needle device. Commonly, the vaccine can be administered as a single dose, or its components can also be administered in combination at the same time or at different times.

The inventors of the present disclosure unexpectedly found that the combination of the above two adjuvants and gE protein shows surprisingly high immunological activity. Therefore, the vaccine composition of the present disclosure becomes a new generation of varicella zoster vaccine.

Other aspects of the present disclosure are obvious to those skilled in the art due to the disclosure herein.

DETAILED DESCRIPTION OF THE EMBODIMENTS

Example 1: Preparation of Vaccine Composition Containing VZV gE Antigen Protein

In order to study the technical effects of the vaccine composition provided by the present disclosure, the inventors of the present disclosure prepared the following vaccine composition formulations (0.5 ml/dose), each of which contains VZV gE protein, an aluminum adjuvant, and a CpG ODN adjuvant. The specific preparation method included: firstly adsorbing a gE antigen stock solution onto an aluminum adjuvant (aluminum phosphate adjuvant) to prepare adsorption samples with different ratios of gE antigen/aluminum adjuvant (w/w) (where the aluminum adjuvant content was substantially the content of aluminum element); and then adding CpG ODN samples (CpG 7909) of different concentrations to the gE antigen/aluminum adsorption samples. After the above formulations were thoroughly mixed, if not administrated immediately, they were stored at 4° C. The specific ratios were as follows.

TABLE 1

| No. | gE (μg) | Aluminum adjuvant (μg) | CpG ODN adjuvant (μg) | Volume (μl) |
|---|---|---|---|---|
| 1 | 10 | 600 | 300 | 500 |
| 2 | 10 | 600 | 600 | 500 |
| 3 | 10 | 600 | 900 | 500 |
| 4 | 10 | 600 | 1200 | 500 |
| 5 | 50 | 600 | 300 | 500 |
| 6 | 50 | 600 | 600 | 500 |
| 7 | 50 | 600 | 900 | 500 |
| 8 | 50 | 600 | 1200 | 500 |
| 9 | 100 | 600 | 300 | 500 |
| 10 | 100 | 600 | 600 | 500 |
| 11 | 100 | 600 | 900 | 500 |
| 12 | 100 | 600 | 1200 | 500 |
| 13 | 0 | 600 | 1200 | 500 |
| 14 | 10 | 225 | 600 | 500 |
| 15 | 50 | 225 | 600 | 500 |
| 16 | 100 | 225 | 600 | 500 |

Example 2

For the obtained recombinant herpes zoster vaccine composition to be evaluated of Example 1, the inventors carried out immunogenicity studies using C57BL/6 mice as animal models. The immunogenicity of the vaccine composition provided by the present disclosure was investigated using gE protein as antigen and an aluminum adjuvant and CpG ODN as adjuvants. 6-8 weeks old C57BL/6 mice were randomly divided into groups, 10 mice in each group. The vaccine prepared using gE protein in combination with adjuvants is intramuscularly injected. A vaccine group and an adjuvant group were set. Immunization was performed at weeks 0 and 3, and blood and spleens were collected at week 5. The ELISA method was used to detect the titer of the anti-VZV gE protein binding antibody in serum, namely total IgG, and the ELISPOT method was used to detect the cellular immunity level, mainly expression of IFN-γ, in spleen cells. It should be noted that in addition to the above-mentioned 16 groups of experiments, parallel experiments with the same ratios were conducted in the present disclosure without changing other parameters and procedures to verify the effect of the vaccine composition composed of 1018 of CpG ODN, VZV gE protein, and an aluminum adjuvant. The data finally obtained showed that the IgG (GMT) value thereof is substantially the same as the value in the case of CpG 7909, and the IFN-γ value thereof is slightly lower than the value in the case of CpG 1018, but there is no significant difference. For example, for group 3, when CpG ODN is CpG 7909, the IFN-γ value is 24, for group 4, the IFN-γ value is 30, and for groups 9-11, the IFN-γ values are 120, 125, and 102.

The evaluation method for immunogenicity is a conventional technical means in the art. As an example, the more specific operations are as follows.

1. Animal Experiment of Recombinant Herpes Zoster Vaccine 6-8 weeks old C57BL/6 mice were selected and randomly divided into groups, 10 mice in each group. Vaccines of different dosages (Table 1) were intraperitoneally injected with an injection volume of 0.05 ml. Immunization was performed at weeks 0 and 3, and blood and spleens were collected at week 5. Serum was separated for ELISA to detect binding antibody titer, and splenic lymphocytes were separated for ELISPOT analysis.

2. Binding Antibody Titer Detection

Serum was collected 2 weeks after the second immunization of mice, and the titer of anti-gE protein binding antibody was detected.

(1) The antigen gE stock solution was diluted with PBS to 1 μg/ml, and 100 μl of the diluted stock solution was added to each well of an ELISA plate. The plate was stored at 4° C. overnight and washed by a plate washer.

(2) 5% skimmed milk was prepared with PBS, and 100 μl of skimmed milk was added to each well of the ELISA plate. The plate was maintained at 37° C. for 2 hours and washed by a plate washer.

(3) 2% skimmed milk was prepared with PBS, the serum to be tested was gradiently diluted, and 100 μl of diluted serum was added to each well of the ELISA plate. The plate was maintained at 37° C. for 1 hour and washed by a plate washer.

(4) The goat anti-mouse antibody was diluted with 2% skimmed milk in PBS at a ratio of 1:10000, and 100 μl of secondary antibody diluted with skimmed milk was added to each well of the ELISA plate. The plate was maintained at 37° C. for 1 hour and washed by a plate washer.

(5) A chromogenic solution was prepared in a proportion of 9 ml of chromogenic buffer, 1 ml of TMB, and 10 μl of 3% $H_2O_2$. 100 μl of the chromogenic solution was added to each well of the ELISA plate. The plate was maintained at 37° C. for 10 min and washed by a plate washer.

(6) Reading is performed at 450 nm/620 nm.

3. Cellular Immunoassay

At two weeks after the second immunization of mice, spleens were taken from each group of mice, and lymphocytes were separated. The level of IFN-γ expressed by mouse splenic lymphocytes (n=2) was assessed by ELISPOT.

(1) ELISPOT Plate Coating (Sterile Operation, Performed the Day Before Removing the Spleen)

The ELISPOT plate was wetted with 35% alcohol, wherein an amount of 15 μl/well of alcohol was added to a 96-well ELISPOT plate and maintained for a retention time of no more than 1 minute. 200 μl/well sterile water was added to wash the plate 5 times. 150 μl of IFN-γ coating antibody was added to 10 ml PBS, mixed thoroughly, and filtered by a 0.2-μm filter membrane. The diluted coating antibody solution was added to the 96-well ELISPOT plate in an amount of 100 μl/well and stored at 4° C. overnight.

(2) ELISPOT Plate Sealing (Sterile Operation)

The coating antibody was discarded, 200 μl/well of sterile PBS was added to wash the plate 5 times. A 1640 complete medium (containing 10% FBS) was added to the 96-well ELISPOT plate in an amount of 200 μl/well, and the plate was sealed at room temperature for more than 30 minutes. Liquid was discarded, and water was removed as much as possible by inverting the plate on a sterilized gauze to avoid air bubbles when a medium was added in a subsequent step.

(3) Lymphocyte Preparation (Sterile Operation)

Mice were sacrificed and immersed in 75% ethanol. The mouse spleen was taken out in a clean bench. A burned 200-mesh copper screen was placed into a 35 mm culture dish, 1 ml of a lymphocyte separation solution was added, and grinding is performed with a plunger of a 1-ml syringe. The separation solution in which spleen cells are suspended was filtered through the burned 200-mesh copper screen and transferred to a 15-ml centrifuge tube, the lymphocyte separation solution was added therein to 4 ml, and 0.5 ml of RPMI1640 basal medium was added to cover the liquid surface. It was room temperature, 800 g, acceleration 3, centrifugation 30 minutes. The lymphocyte layer was sucked out, and then added with 10 ml RPMI1640 basal medium, and subjected to washing, at room temperature, with centrifugation of 250 g, 10 minutes. The supernatant was discarded, 2 ml RPMI1640 complete medium was added to resuspend the cells, and the cells were counted.

(4) Sample Addition (Sterile Operation)

Addition of cells: the cells were diluted with a complete medium to $6×10^6$/ml according to cell count results, and meanwhile, 1000 times dilution of mAb CD28-A was added to the cell suspension. 100 μl/well of the cell suspension was added to the ELISPOT plate. Positive control: 1 μl of ConA stimulant was added, and a stimulation concentration was 5 μg/ml. Sample to be tested: stimulant gE protein peptide library diluted with serum-free medium was added to a final concentration of 2 μg/ml, Negative control: neither ConA stimulant nor stimulant short peptide was added. They were incubated at 37° C. and 5% $CO_2$ for 24 hours, during which the culture plate should not be moved to avoid changes in cell position and the resulting blur of ELISPOT spots.

(5) Spot Detection

The cell suspension was discarded, and 200 μl/well of sterile PBS was added to wash the plate 5 times. 50 μl of biotin-labeled detection antibody was added to 10 ml diluent (PBS+0.1% BSA), mixed thoroughly, and filtered by a 0.2-μm filter membrane. 100 μl of the detection antibody dilution was added to each well and incubated at 37° C. for 2 hours. The biotin-labeled detection antibody dilution was discarded, and 200 μl/well of sterile PBS was added to wash the plate 5 times. The antibody was diluted with a diluent (PBS+0.1% BSA), 50 μl of the antibody was added with 10 ml of the diluent, mixed thoroughly, and filtered by a 0.2-μm filter membrane. 100 μl of the dilution was added to each well and incubated at 37° C. for 1 hour. The operations from this step should be conducted in a dark place. The antibody dilution was discarded, and 200 μl/well of sterile PBS was added to wash the plate 5 times. Fluorescence enhancer-II was added to the 96-well ELISPOT plate in an amount of 50 μl/well, and incubation was performed at 37° C. for 15 minutes. The liquid in the plate was discarded, the plate was inverted on absorbent paper and patted to remove the small drops of water. The protective layer was removed, the plate was placed in an electric thermostat incubator, and the film was dried at 37° C. in a dark place. The ELISPOT plate was placed in CTL-ImmunoSpot® S5 VersC CnClyzer, an enzyme-linked spot image automatic analyzer, for which parameters were appropriately adjusted for performing spot counting.

The specific results are shown in Table 2 below.

TABLE 2

Summary of results of investigation on proportions of antigen, aluminum adjuvant, and CpG ODN adjuvant (7909)

| No. | gE (μg) | Aluminum adjuvant (μg) | CpG ODN adjuvant (μg) | Injection volume (μl) | IgG (GMT) | IFN-γ (Number of positive cells per million spleen cells) |
|---|---|---|---|---|---|---|
| 1 | 10 | 600 | 300 | 50 | 1:4095000 | 73 |
| 2 | 10 | 600 | 600 | 50 | 1:1236000 | 43 |
| 3 | 10 | 600 | 900 | 50 | 1:2297000 | 72 |
| 4 | 10 | 600 | 1200 | 50 | 1:2178000 | 54 |
| 5 | 50 | 600 | 300 | 50 | 1:2702000 | 128 |
| 6 | 50 | 600 | 600 | 50 | 1:2169000 | 139 |
| 7 | 50 | 600 | 900 | 50 | 1:2862000 | 86 |
| 8 | 50 | 600 | 1200 | 50 | 1:2345000 | 91 |
| 9 | 100 | 600 | 300 | 50 | 1:4000000 | 157 |
| 10 | 100 | 600 | 600 | 50 | 1:2297000 | 175 |
| 11 | 100 | 600 | 900 | 50 | 1:2862000 | 183 |
| 12 | 100 | 600 | 1200 | 50 | 1:3194000 | 121 |
| 13 | 0 | 600 | 1200 | 50 | 1:100 | 3 |
| 14 | 10 | 225 | 600 | 50 | 1:1888000 | 61 |
| 15 | 50 | 225 | 600 | 50 | 1:2551000 | 100 |
| 16 | 100 | 225 | 600 | 50 | 1:1764000 | 152 |

TABLE 3

Summary of results of investigation on proportions of antigen, aluminum adjuvant, and CpG1018

| No. | gE (μg) | Aluminum adjuvant (μg) | CpG 1018 adjuvant (μg) | Injection volume (μl) | IgG (GMT) | IFN-γ (Number of positive cells per million spleen cells) |
|---|---|---|---|---|---|---|
| 1 | 10 | 600 | 300 | 50 | 1:1888000 | 80 |
| 2 | 10 | 600 | 900 | 50 | 1:2551000 | 24 |
| 3 | 10 | 600 | 1200 | 50 | 1:1764000 | 30 |
| 4 | 100 | 600 | 300 | 50 | 1:4095000 | 120 |
| 5 | 100 | 600 | 900 | 50 | 1:2491000 | 125 |
| 6 | 100 | 600 | 1200 | 50 | 1:1037000 | 102 |
| 7 | 0 | 600 | 1200 | 50 | 1:100 | 6 |

It can be seen from Tables 2-3 that the vaccine composition prepared according to the specific compositions and ratios provided by the present disclosure has good immune activity, and especially when the content of gE protein is 50-100 μg, the content of the aluminum adjuvant is 225-600 μg, and the content of the CpG ODN adjuvant is 300-900 μg, the vaccine composition has excellent cellular immunity effect and can be used as a new generation of vaccine composition.

All the documents mentioned in the present disclosure are cited as references in this application, as if each document was individually cited as a reference. In addition, it should be understood that after reading the above teaching content of the present disclosure, those skilled in the art can make various changes or modifications to the present disclosure, and these equivalent forms also fall within the scope defined by the appended claims of the present application.

The invention claimed is:

1. A recombinant herpes zoster vaccine composition, comprising gE protein of varicella zoster virus (VZV) and a pharmaceutically acceptable combined adjuvant, wherein the pharmaceutically acceptable combined adjuvant is an aluminum adjuvant combined with a CpG adjuvant, a content of the gE protein is 50-100 μg, a content of the aluminum adjuvant is 225-600 μg, and a content of the CpG adjuvant is 300-900 μg.

2. A method for preventing diseases associated with herpes zoster virus infection, comprising administrating the recombinant herpes zoster vaccine composition according to claim 1.

3. A kit, comprising the recombinant herpes zoster vaccine composition according to claim 1, wherein the kit comprises a vaccine administration device, and the administration device comprises a needle device, a liquid ejection device, a powder device, and a spray device.

4. The vaccine composition according to claim 1, wherein the CpG adjuvant is CPG 1018 or CPG 7909.

* * * * *